US00PP27530P2

(12) United States Plant Patent
Delabroye

(10) Patent No.: US PP27,530 P2
(45) Date of Patent: Jan. 3, 2017

(54) ***HEUCHERA* PLANT NAMED 'PINK PEARLS'**

(50) Latin Name: ***Heuchera* hybrid**
Varietal Denomination: Pink Pearls

(71) Applicant: Thierry Delabroye, Hantay (FR)

(72) Inventor: Thierry Delabroye, Hantay (FR)

(73) Assignee: Sandrine Delabroye, Hantay (FR)

( * ) Notice: Subject to any disclaimer, the term of this patent is extended or adjusted under 35 U.S.C. 154(b) by 74 days.

(21) Appl. No.: 14/121,865

(22) Filed: Oct. 28, 2014

(51) Int. Cl.
*A01H 5/12* (2006.01)

(52) U.S. Cl.
USPC ..... Plt./440

(58) Field of Classification Search
USPC ..... Plt./440
See application file for complete search history.

(56) References Cited

PUBLICATIONS

CNB New Plants Catalogue *Heuchera* 'Pink Pearls', retrieved on Mar. 28, 2016, retrieved from the Internet at <http://www.cnb.nl/EN/Pages/Product-Catalog.aspx?ProductId=219> one page.*

* cited by examiner

*Primary Examiner* — June Hwu
(74) *Attorney, Agent, or Firm* — Penny J. Aguirre

(57) ABSTRACT

A new cultivar of *Heuchera* named 'Pink Pearls' that is characterized by its compact and mounded plant habit, its leaves that are bronze-orange in color, its very floriferous and long blooming habit, and its large pink flowers on dark magenta flowering stems.

2 Drawing Sheets

Botanical classification: *Heuchera* hybrid.
Cultivar designation: 'Pink Pearls'.

BACKGROUND OF THE INVENTION

The present invention relates to a new and distinct cultivar of *Heuchera* of hybrid origin, botanically known as a *Heuchera* and is hereinafter referred to by its cultivar name 'Pink Pearls'.

The new cultivar was discovered as a chance seedling in a trial field by the Inventor in Hantay, France in April of 2011. The trial field contained hundreds of proprietary *Heuchera* seedlings from the Inventor's breeding program. The exact parentage of 'Pink Pearls' is therefore unknown.

Asexual propagation of the new cultivar was first accomplished under the direction of the Inventor by in vitro propagation initiated from meristem tissue in Rijswijk, The Netherlands in September of 2012. Asexual propagation of the new cultivar by in vitro propagation has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Pink Pearls' as a new and unique cultivar of *Heuchera*.

1. 'Pink Pearls' exhibits a compact and mounded plant habit.
2. 'Pink Pearls' exhibits leaves that are bronze-orange in color.
3. 'Pink Pearls' exhibits a very floriferous and long blooming habit.

4. 'Pink Pearls' exhibits large pink flowers on dark magenta flowering stems.

'Pink Pearls' can be most closely compared to the *Heuchera* cultivars 'Apricot' (U.S. Plant Pat. No. 27,139) and 'Brown Sugar' (U.S. Plant Pat. No. 25,647). 'Apricot' differs from 'Pink Pearls' in having flowers that are darker pink in color and in having foliage that is pink-apricot to orange in color with some silvery overlay in the leaf centers. 'Brown Sugar' is similar to 'Pink Pearls' in having a very floriferous bloom habit. 'Brown Sugar' differs from 'Pink Pearls' in having leaves that are darker brownish-green in color and in having flowers that are lighter pink in color.

BRIEF DESCRIPTION OF THE DRAWINGS

The accompanying colored photographs illustrate the overall appearance and distinct characteristics of the new *Heuchera*. The photographs were taken of a plant one year in age as grown in a greenhouse in a 23-cm container in Hillegom, The Netherlands.

The photograph in FIG. 1 provides a side view of the plant habit of 'Pink Pearls' in bloom.

Figure 1:
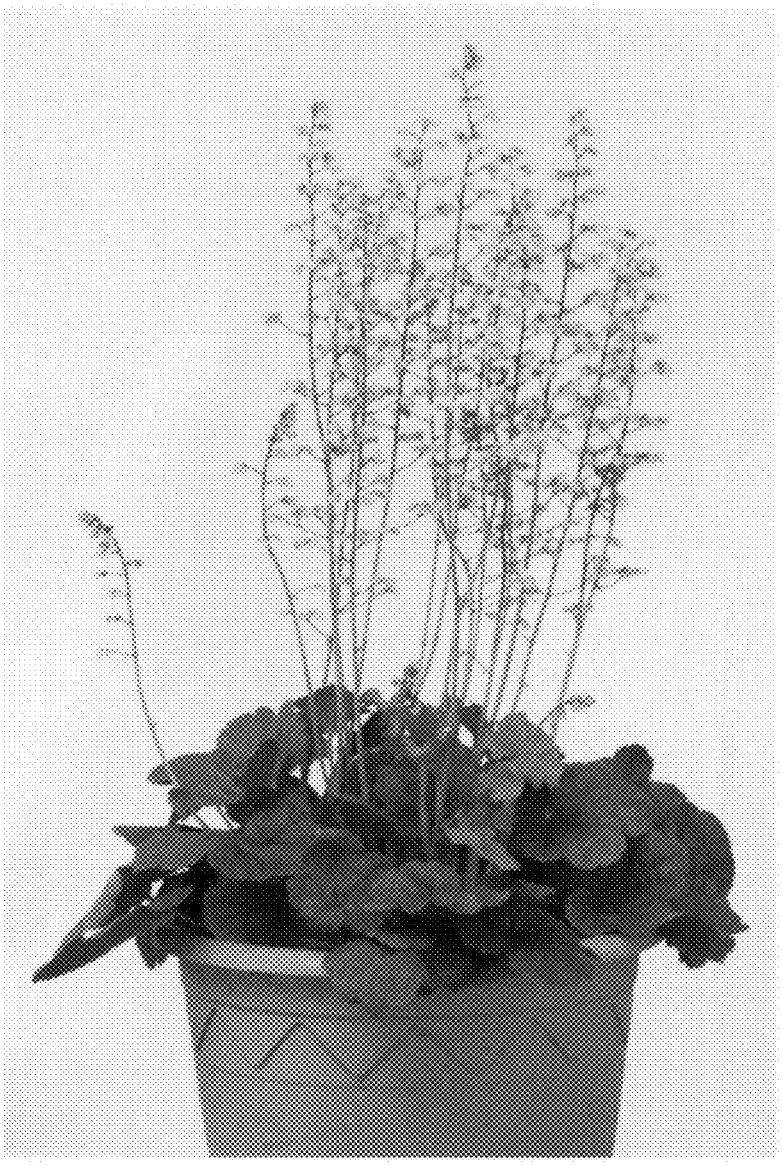
Figure 2:
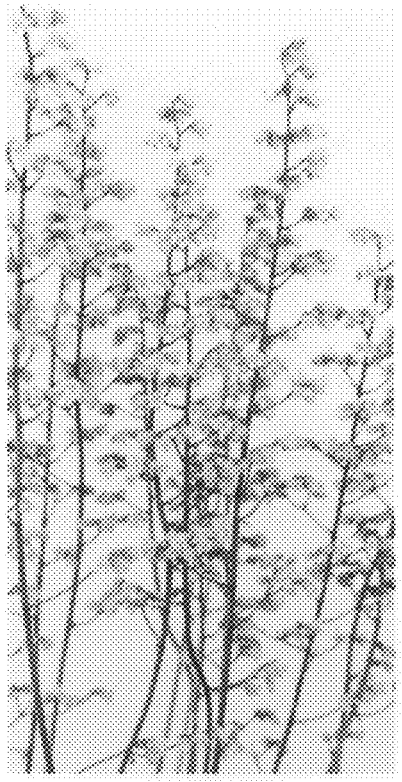

The photograph in FIG. 2 provides a close-up view of the inflorescences of 'Pink Pearls'.

Figure 3:
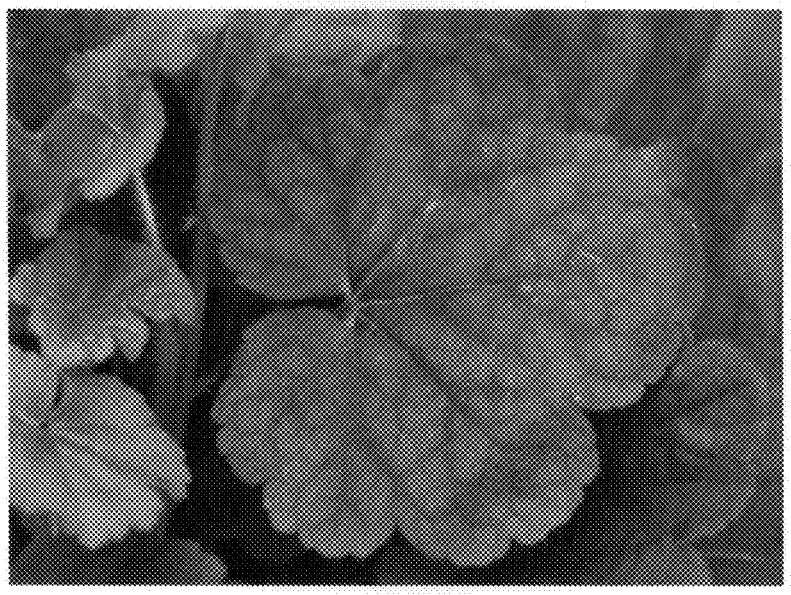

The photograph in FIG. 3 provides a close-up view of the young (left) and mature (center) leaves of 'Pink Pearls'.

The colors in the photographs are as close as possible with the digital photography techniques available, the color values cited in the detailed botanical description accurately describe the colors of the new *Heuchera*.

DETAILED BOTANICAL DESCRIPTION OF THE PLANT

The following is a detailed description of one-year old plants of the new cultivar as grown in a greenhouse in 23-cm containers in Hillegom, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Long blooming; an average of 8 weeks from late spring into summer in The Netherlands.

*Plant type*.—Herbaceous perennial.

*Plant habit*.—Compact and mounded.

*Height and spread*.—An average of 50 cm in height (including inflorescences) and 35 cm in width as a one year-old plant.

*Hardiness*.—At least in U.S.D.A. Zones 3 to 9.

*Diseases and pests*.—Not unique susceptibility/resistance to pests or diseases has been observed.

*Root description*.—Fibrous roots on woody rootstalks.

*Propagation*.—In vitro propagation.

*Growth rate*.—Moderate.

Stem description (peduncle, flowering stem):

*Shape*.—Round.

*Stem color*.—185A to 185B.

*Stem size*.—An average of 2 mm in diameter and 40.1 cm in length (22 cm from base to apex of inflorescence.

*Stem strength*.—Moderate.

*Stem aspect*.—Flowering stems grow at an average angle of 80° to base (0°=horizontal).

*Stem surface*.—Densely covered with short hairs, average of 0.75 mm in length, NN155D in color.

*Stem number*.—Average of 56 flowering stems.

*Branching habit*.—Flowering stems emerge from basal rosette.

Foliage description:

*Leaf shape*.—Orbicular.

*Leaf division*.—Simple.

*Leaf base*.—Hastate, touching to moderately overlapping.

*Leaf apex*.—Obtuse with tip mucronate.

*Leaf venation*.—Laciniate, color; young leaf upper and lower surface a blend between 174D and 181D, mature leaf upper surface 152A with secondary and tertiary veins a blend between 200A and N186A and lower surface 184D, lower surface main vein sparsely covered with short hairs 1.5 mm in length and NN155D in color.

*Leaf margins*.—Lobed with average of 5 lobes per leaf, shallow lobe depth, lobe margins bi-crenate and very weakly undulate, moderately covered with short hairs 1.5 mm in length and NN155D in color.

*Leaf attachment*.—Petiolate.

*Leaf arrangement*.—Alternate in basal rosettes.

*Leaf orientation*.—Typically nearly horizontal to petiole and slightly cupped.

*Leaf surface*.—Upper surface; very slightly glossy and glabrous, lower surface; very slightly glossy and sparsely pubescent on main veins.

*Leaf color*.—In the spring and early summer, young leaves upper surface; a blend between 166B and 183C to 183D tinged with 199A towards the margins and lower surface; 184C, mature and fall leaves upper surface; 200B to 200C and tinged with a blend between 148A and N199A, mature and fall leaves lower surface; a blend between N77B and N186D color deepens in the late summer and fall.

*Leaf size*.—An average of 8.7 cm in length and 9.1 cm in width.

*Leaf quantity*.—An average of 16 per basal rosette.

*Petioles*.—An average of 11.8 cm in length and 2 mm in diameter, color; 177A with base 178A, surface; densely covered with soft hairs an average of 2.5 mm in length and NN155D in color.

*Stipules*.—Small leafy stipules at the base of each leaf, narrow acute apex, an average of 1.1 cm in length and 3 mm in width, color; 155A with base 70B.

Flower description:

*Inflorescence type*.—Numerous small bell-shaped flowers arranged on panicles on peduncles emerging from the base of the rosette.

*Inflorescence size*.—An average of 21 cm in height (excluding peduncle) and 5.0 cm in width.

*Inflorescence number*.—An average of 90 in a 23-cm container.

*Flower fragrance*.—None.

*Flower quantity*.—Average of 180 flowers per flowering stem.

*Flower lastingness*.—Average of one week.

*Flower buds*.—Oblong in shape, an average of 5 mm in diameter and 2 mm in diameter, 62A to 62B in color.

*Flower attitude*.—Outwards to slightly nodding.

*Flower type*.—Single, campanulate.

*Flower size*.—About 6 mm in length and 7 mm in diameter.

*Petals*.—About 5, rotate arrangement and implanted in the hypanthium at base, oblanceolate in shape, margin is entire, apex is acute, upper and lower surface is dull and glabrous, color of upper and lower surface when opening and when fully open; 69D with base 68C to 68D, an average of 4.5 mm in length and 1 mm in width.

*Calyx*.—Campanulate, sepals fused to hypanthium, 6 mm in length and diameter.

*Sepals*.—An average of 5, fused into campanulate hypanthium, oblong in shape, an average of 6 mm in length and 2 mm in width, margin is entire and fused into hypanthium, apex is obtuse, fused base, color; immature and mature upper surface; 62A to 62B, immature and mature lower surface; a blend between 61D and 62 with base 61D, surfaces are dull, lower surface is moderately covered with very short glandular hairs an average of .25 mm in length and a blend between N155B and 69D in color.

*Pedicels*.—An average of 3.5 mm in length and 0.5 mm in diameter, 185A in color, moderate strength, average angle of 40° (0°=horizontal).

Reproductive organs:

*Gynoecium*.—An average of 2 pistils, 4 mm in length, stigma; pointed in shape, NN155D in color, style; an average of 3.5 mm in length and 155A in color, ovary; 155A in color.

*Androcoecium*.—An average of 5 stamens, anthers; ovate in shape, about 0.5 mm in length and 156A in color, filament; 3.5 mm in length and NN155A in color, pollen; low in quantity and 155A in color.

*Seed/fruit*.—No fruit or seeds were observed.

It is claimed:

1. A new and distinct cultivar of *Heuchera* plant named 'Pink Pearls' as herein illustrated and described.

* * * * *